(12) United States Patent
Kim et al.

(10) Patent No.: US 6,916,973 B2
(45) Date of Patent: Jul. 12, 2005

(54) NUCLEIC ACID MOLECULES ENCODING HYPERACTIVE MUTANT PHYTOCHROMES AND USES THEREOF

(75) Inventors: Jeong Il Kim, Kwangju (KR); Pill Soon Song, Kwangju (KR); Ki Young Yang, Kwangju (KR); Moon Soo Soh, Kwangju (KR); Chung Mo Park, Kwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 409 days.

(21) Appl. No.: 10/134,500

(22) Filed: Apr. 30, 2002

(65) Prior Publication Data

US 2003/0204872 A1 Oct. 30, 2003

(51) Int. Cl.[7] .................. C12N 15/29; C12N 15/82; C12N 15/87; A01H 1/00
(52) U.S. Cl. .................. 800/298; 800/290; 435/320.1; 435/468; 536/23.1; 536/23.6
(58) Field of Search .................. 800/298, 290, 800/278, 287; 435/320.1, 468, 419; 536/23.1, 23.6

(56) References Cited

PUBLICATIONS

Casal et al (2002 Plant Physiology 129:1127–1137).*
Hershey et al (1993, NCBI Accession No. X03242).*
Bowie et al, Science 247:1306–1310, 1990.*
McConnell et al, Nature 411 (6838):709–713, 2001.*
Smith et al, Plant, Cell and Envir. 20, 1997, pp. 840–844, The shade avoidance syndrome: multiple responses mediated by.
Neff et al, Genes & Development, 14, 2000, pp. 257–271, Light: an indicator of time and place.
Yeh et al, Proc. Natl. Acad. Sci., vol. 95, pp. 13976–13981, Nov. 1998, Eukaryotic phytochromes: Light–regulated serine.
Lapko et al, Protein Science 8, 1999, pp. 1032–1044, Mass spectrometric characterization of oat phytochrome A: Isoforms.
Park et al, Cell & Devlopment Biol., vol. 11, 2000, pp. 449–456 Inter–domain crosstalk in the phytochrome molecules.
Lapko et al, Biochemistry 36, 1997, pp. 10595–10599, Post–translational Modification of Oat Phytochrome A:.
Bhoo et al, J. Am. Chem. Soc. 119, 1997, pp. 11717–11718, Phytochrome Photochromism Probed by Site–Directed Mutations.
Fankhauser et al, SCIENCE, vol. 284, May 28, 1999, pp. 1539–1541, PKS1, a Substrate Phosphorylated by Phytochrome That.
Quail et al, SCIENCE, vol. 268, May 5, 1995, pp. 675–680, Phyto–chromes: Photosensory Perception and Signal Transduction.
Shinomura et al, Proc. Natl. Acad. Sci, vol. 93, pp. 8129–8133 Action spectra for phytochrome A– and B–specific.
Boylan et al, Proc. Natl. Acad. Sci., vol. 88, pp. 10806–10810, Dec. 1991, Phytochrome A overexpression inhibits hypocotyl.

* cited by examiner

*Primary Examiner*—Amy J. Nelson
*Assistant Examiner*—Stuart F. Baum
(74) *Attorney, Agent, or Firm*—Jacobson Holman PLLC (57) ABSTRACT

The present invention includes modified phytochrome A (PHYA) nucleic acid molecules in which DNA sequences coding for "active site" amino acid residues have been mutated to generate hyperactive phytochromes. In particular; a serine/threonine residue at the hinge between the N- and C-terminal domains as well as at the N-terminal serine/threonine cluster of phytochromes (e.g., serine-598 and serine-7 in oat phytochrome A) for (a) Pr/Pfr-dependent phosphorylation and (b) dephosphorylation by a phytochrome phosphatase (PP2A) was substituted with alanine. (c) In addition, amino acid residues within the phytochrome chromophore pocket are mutated to generate the bathchromic shift of the Pr-absorption band of both wild type and above-mentioned mutant phytochromes. The plants with the bathchromically shifted absorption spectrum are expected to respond to the canopy and shade conditions for growth and greening responses to far-red light with greater efficiency than are the wild type plants with normal absorption band maxima. These mutative modifications confer hyperactivity to the far-red light responsive phytochromes A. Thus, the biological activity of the modified oat PHYA was shown to be hyperactive compared to wild type PHYA, characterized by its ability to reduce internode elongation of adult plants. Overexpression of the phytochrome phosphatase exhibits a suppressed growth with shorter internodes and belated flowering, qualitatively consistent with the phenotype of a ser598ala mutant oat phytochrome. The invention also includes plants having at least one cell expressing the modified PHYA, vectors comprising at least one portion of the modified PHYA nucleic acids, and methods using such vectors for producing plants with reduced stature.

4 Claims, 5 Drawing Sheets

SEQUENCE LISTING

```
<160> NUMBER OF SEQ ID NOS: 8

<210> SEQ ID NO 1
<211> LENGTH: 3510
<212> TYPE: DNA
<213> ORGANISM: Avena sp.
```

-continued

```
<400> SEQUENCE: 1
ccggtagcag caggagcgat acacggggta tacgaccgtt gagtggttca attacttgag      60
gcaggcgatg tcttcctcaa ggcctgcttc cagttcttcc agcaggaacc gccagagctc     120
ccaggcaagg gtgttagcac agacaaccct tgatgccgag ctcaatgctg aatatgaaga     180
atctggtgac tcctttgact actccaagct ggttgaagcc cagcgggatg gtccacctgt     240
gcagcaaggg cggtcggaga aggtcatagc ctacttacag cacattcaga aggaaagct     300 aatccaaaca tttggttgcc tgttggccct tgatgagaag agcttcaatg tcattgcgtt     360
cagcgagaac gcgccagaaa tgcttacaac ggtcagccat gcggtaccca gtgttgatga     420
tcccccaagg ctgggattg gcaccaatgt acggtctctt ttcagtgacc aaggtgccac      480
agcactgcac aaggcactag gatttgctga tgtatctttg ctgaatccta tcctagttca     540
gtgcaagaca tcaggaaagc ctttctatgc cattgttcat cgagcaactg gttgtttggt     600
ggtagacttt gagcctgtaa agcctacaga atttcctgcc actgctgctg ggcttttgca     660
gtcctacaag cttgctgcca aggcaatatc caagatccag tcattgccag gtggaagcat     720
ggagatgcta tgcaatactg tggtgaagga agtctttgac cttaccgggt atgatagggt     780
tatggcttac aagttccatg aagatgacca tggtgaggta ttctccgaaa tcacaaagcc     840
tggtcttgag cctttatctag gcctgcacta tccagccact gatatccctc aagcagccag     900 gtttctttc atgaagaaca aagtacggat gatttgtgat tgccgtgcga gatccataaa     960
ggtcattgaa gctgaggcac tcccctttga tattagccta tgtggttcag cactcagggc    1020
accacacagt tgtcaccttc agtatatgga gaacatgaac tcgattgcat cccttgtcat    1080
ggctgttgtg gttaatgaga atgaagagga tgatgaagct gagtctgaac aaccagcaca    1140
gcagcagaaa aagaagaaac tatggggcct ccttgtttgc caccatgaga gccctagata    1200
tgtccctttt ccgctgcgtt atgcttgtga gttcttagca caggtgtttg ctgtccatgt    1260
caacagggag tttgaattag agaaacagtt gcgtgagaag aacatactga agatgcaaac    1320
aatgctctct gatatgttgt tccgagaagc ctctcccctg actatcgtat cagggaaccc    1380
gaatatcatg gacctagtca aatgtgatgg tgctgctctt ctgtatgggg gcaaagtatg    1440
gcgtctgcgt aatgctccaa cggagtctca gatacatgat atcgccttct ggctatcaga    1500
tgttcacagg gattccactg gcctgagtac tgacagcctc catgatgctg gctatccagg    1560
agctgctgct cttggtgata tgatttgtgg aatggcagtg gctaagatca actccaagga    1620
tattcttttt tggttcaggt cacatacagc tgctgaaatc agatggggag gtgcaaagaa    1680
tgatccatcg gacatggatg acagcagaag gatgcaccct aggttgtctt tcaaagcttt    1740
ccttgaagtt gtcaagatga agagcttgcc ttggagtgac tatgaaatgg atgctattca    1800
ttcattgcaa cttatactgc gagggacact aaatgatgcc agcaagccaa gcgggaagc    1860 tgctctagat aaccagattg gtgatctaaa acttgatggg cttgctgaac tgcaggccgt    1920
gaccagtgaa atggttcgtc taatggaaac agcaactgtt ccaatcttgg cagtagatgg    1980
caatggactg gtcaacgggt ggaatcagaa agcagcggag ttgactgggc taagagttga    2040
tgatgcaatt ggaaggcaca tacttaccct tgtggaggac tcctctgtac cagttgtcca    2100
gaggatgcta tatctagctc tgcagggtaa agaagagaag gaagttcgat ttgaggtaaa    2160
gactcatggc ccgaagaggg atgatggtcc agttatcttg gttgtgaatg cttgtgccag    2220
tcgggacctt catgatcatg ttgttggagt gtgctttgtt gcccaagata tgactgtcca    2280
taagttggtg atggacaagt ttactcgggt tgagggtgac tacaaggcga tcattcacaa    2340
```

-continued

```
cccgaaccca ctcattcctc ctatatttgg tgctgacgaa tttggatggt gttcggagtg    2400
gaatgctgca atgaccaagt tgactgggtg gaatagagat gaagtgctcg ataagatgct    2460
tcttggtgaa gtgtttgaca gtagcaatgc ttcctgccct ttgaagaaca gagatgcatt    2520
tgtaagtctt tgtgttctta tcaacagtgc attagccggg gaagaaacag aaaaggctcc    2580
atttggcttc ttcgacagaa gtggaaagta cattgagtgt cttctatcag caaacagaaa    2640
agaaaatgag ggtggtctca tcactggagt attctgtttt attcatgttg ctagtcatga    2700
gctgcaacat gcactacagg tgcagcaagc ctcggagcaa acgtcgctaa aaaggctcaa    2760
ggctttctcc tacatgagac atgcgatcaa caaccctctc tcaggcatgc tctactctag    2820
aaaagcattg aagaacacag atttgaatga agaacagatg aagcagattc atgttggaga    2880
taattgtcac caccagataa acaagatact gcagacttg gatcaagata gcatcaccga    2940
aaaatctagc tgcttggatt tggagatggc tgaatttctg ttgcaagatg tggtggtggc    3000
tgctgtaagt caagtactga taacctgcca gggaaaaggg atcagaatct cttgcaacct    3060
gccagagaga tttatgaagc agtcagtcta tggagatggt gttcgactcc agcagatcct    3120
ctctgacttc ctgtttattt cagtgaagtt ctctcctgtt ggaggttctg ttgagatttc    3180
ttccaagctg acaaagaaca gcatcggaga aaaccttcat cttattgacc ttgaacttag    3240
gatcaagcac caaggattag gagtcccagc agagctcatg gcacaaatgt ttgaggagga    3300
caacaaggag cagtcagagg agggcttgag cctcctagtt tctagaaacc tgctgaggct    3360
catgaatggt gatgttcggc atctaaggga agctggtgtg tcaaccttca tcatcaccgc    3420
tgaacttgct tccgctccaa cagcaatggg acaatgatga agccagtgga agtgtacaac    3480
ttatggtcat caaatgttct gtttgaattc                                     3510
```

<210> SEQ ID NO 2
<211> LENGTH: 1129
<212> TYPE: PRT
<213> ORGANISM: Avena sp.

<400> SEQUENCE: 2

```
Met Ser Ser Ser Arg Pro Ala Ser Ser Ser Ser Arg Asn Arg Gln
 1               5                   10                  15

Ser Ser Gln Ala Arg Val Leu Ala Gln Thr Thr Leu Asp Ala Glu Leu
                20                  25                  30

Asn Ala Glu Tyr Glu Glu Ser Gly Asp Ser Phe Asp Tyr Ser Lys Leu
            35                  40                  45

Val Glu Ala Gln Arg Asp Gly Pro Pro Val Gln Gln Gly Arg Ser Glu
        50                  55                  60

Lys Val Ile Ala Tyr Leu Gln His Ile Gln Lys Gly Lys Leu Ile Gln
 65                  70                  75                  80

Thr Phe Gly Cys Leu Leu Ala Leu Asp Glu Lys Ser Phe Asn Val Ile
                    85                  90                  95

Ala Phe Ser Glu Asn Ala Pro Glu Met Leu Thr Thr Val Ser His Ala
                100                 105                 110

Val Pro Ser Val Asp Asp Pro Arg Leu Gly Ile Gly Thr Asn Val
            115                 120                 125

Arg Ser Leu Phe Ser Asp Gln Gly Ala Thr Ala Leu His Lys Ala Leu
        130                 135                 140

Gly Phe Ala Asp Val Ser Leu Leu Asn Pro Ile Leu Val Gln Cys Lys
145                 150                 155                 160
```

-continued

```
Thr Ser Gly Lys Pro Phe Tyr Ala Ile Val His Arg Ala Thr Gly Cys
            165                 170                 175

Leu Val Val Asp Phe Glu Pro Val Lys Pro Thr Glu Phe Pro Ala Thr
            180                 185                 190

Ala Ala Gly Ala Leu Gln Ser Tyr Lys Leu Ala Lys Ala Ile Ser
            195                 200                 205

Lys Ile Gln Ser Leu Pro Gly Gly Ser Met Glu Met Leu Cys Asn Thr
            210                 215                 220

Val Val Lys Glu Val Phe Asp Leu Thr Gly Tyr Asp Arg Val Met Ala
225                 230                 235                 240

Tyr Lys Phe His Glu Asp Asp His Gly Glu Val Phe Ser Glu Ile Thr
            245                 250                 255

Lys Pro Gly Leu Glu Pro Tyr Leu Gly Leu His Tyr Pro Ala Thr Asp
            260                 265                 270

Ile Pro Gln Ala Ala Arg Phe Leu Phe Met Lys Asn Lys Val Arg Met
            275                 280                 285

Ile Cys Asp Cys Arg Ala Arg Ser Ile Lys Val Ile Glu Ala Glu Ala
            290                 295                 300

Leu Pro Phe Asp Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
            325                 330                 335

Val Met Ala Val Val Val Asn Glu Asn Glu Glu Asp Glu Ala Glu
            340                 345                 350

Ser Glu Gln Pro Ala Gln Gln Lys Lys Lys Leu Trp Gly Leu
            355                 360                 365

Leu Val Cys His His Glu Ser Pro Arg Tyr Val Pro Phe Pro Leu Arg
            370                 375                 380

Tyr Ala Cys Glu Phe Leu Ala Gln Val Phe Ala Val His Val Asn Arg
385                 390                 395                 400

Glu Phe Glu Leu Glu Lys Gln Leu Arg Glu Lys Asn Ile Leu Lys Met
            405                 410                 415

Gln Thr Met Leu Ser Asp Met Leu Phe Arg Glu Ala Ser Pro Leu Thr
            420                 425                 430

Ile Val Ser Gly Asn Pro Asn Ile Met Asp Leu Val Lys Cys Asp Gly
            435                 440                 445

Ala Ala Leu Leu Tyr Gly Gly Lys Val Trp Arg Leu Arg Asn Ala Pro
450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
            485                 490                 495

Pro Gly Ala Ala Ala Leu Gly Asp Met Ile Cys Gly Met Ala Val Ala
            500                 505                 510

Lys Ile Asn Ser Lys Asp Ile Leu Phe Trp Phe Arg Ser His Thr Ala
            515                 520                 525

Ala Glu Ile Arg Trp Gly Gly Ala Lys Asn Asp Pro Ser Asp Met Asp
            530                 535                 540

Asp Ser Arg Arg Met His Pro Arg Leu Ser Phe Lys Ala Phe Leu Glu
545                 550                 555                 560

Val Val Lys Met Lys Ser Leu Pro Trp Ser Asp Tyr Glu Met Asp Ala
            565                 570                 575
```

-continued

```
Ile His Ser Leu Gln Leu Ile Leu Arg Gly Thr Leu Asn Asp Ala Ser
            580                 585                 590

Lys Pro Lys Arg Glu Ala Ala Leu Asp Asn Gln Ile Gly Asp Leu Lys
            595                 600                 605

Leu Asp Gly Leu Ala Glu Leu Gln Ala Val Thr Ser Glu Met Val Arg
    610                 615                 620

Leu Met Glu Thr Ala Thr Val Pro Ile Leu Ala Val Asp Gly Asn Gly
625                 630                 635                 640

Leu Val Asn Gly Trp Asn Gln Lys Ala Ala Glu Leu Thr Gly Leu Arg
                645                 650                 655

Val Asp Asp Ala Ile Gly Arg His Ile Leu Thr Leu Val Glu Asp Ser
            660                 665                 670

Ser Val Pro Val Val Gln Arg Met Leu Tyr Leu Ala Leu Gln Gly Lys
            675                 680                 685

Glu Glu Lys Glu Val Arg Phe Glu Val Lys Thr His Gly Pro Lys Arg
        690                 695                 700

Asp Asp Gly Pro Val Ile Leu Val Val Asn Ala Cys Ala Ser Arg Asp
705                 710                 715                 720

Leu His Asp His Val Val Gly Val Cys Phe Val Ala Gln Asp Met Thr
                725                 730                 735

Val His Lys Leu Val Met Asp Lys Phe Thr Arg Val Glu Gly Asp Tyr
            740                 745                 750

Lys Ala Ile Ile His Asn Pro Asn Pro Leu Ile Pro Pro Ile Phe Gly
            755                 760                 765

Ala Asp Glu Phe Gly Trp Cys Ser Glu Trp Asn Ala Ala Met Thr Lys
            770                 775                 780

Leu Thr Gly Trp Asn Arg Asp Glu Val Leu Asp Lys Met Leu Leu Gly
785                 790                 795                 800

Glu Val Phe Asp Ser Ser Asn Ala Ser Cys Pro Leu Lys Asn Arg Asp
                805                 810                 815

Ala Phe Val Ser Leu Cys Val Leu Ile Asn Ser Ala Leu Ala Gly Glu
                820                 825                 830

Glu Thr Glu Lys Ala Pro Phe Gly Phe Phe Asp Arg Ser Gly Lys Tyr
        835                 840                 845

Ile Glu Cys Leu Leu Ser Ala Asn Arg Lys Glu Asn Glu Gly Gly Leu
850                 855                 860

Ile Thr Gly Val Phe Cys Phe Ile His Val Ala Ser His Glu Leu Gln
865                 870                 875                 880

His Ala Leu Gln Val Gln Gln Ala Ser Glu Gln Thr Ser Leu Lys Arg
                885                 890                 895

Leu Lys Ala Phe Ser Tyr Met Arg His Ala Ile Asn Asn Pro Leu Ser
            900                 905                 910

Gly Met Leu Tyr Ser Arg Lys Ala Leu Lys Asn Thr Asp Leu Asn Glu
        915                 920                 925

Glu Gln Met Lys Gln Ile His Val Gly Asp Asn Cys His His Gln Ile
    930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
                965                 970                 975

Val Ala Ala Val Ser Gln Val Leu Ile Thr Cys Gln Gly Lys Gly Ile
            980                 985                 990
```

```
Arg Ile Ser Cys Asn Leu Pro Glu Arg Phe Met Lys Gln Ser Val Tyr
        995                 1000                1005
Gly Asp Gly Val Arg Leu Gln Gln Ile Leu Ser Asp Phe Leu Phe Ile
    1010                1015                1020
Ser Val Lys Phe Ser Pro Val Gly Gly Ser Val Glu Ile Ser Ser Lys
1025                1030                1035                1040
Leu Thr Lys Asn Ser Ile Gly Glu Asn Leu His Leu Ile Asp Leu Glu
        1045                1050                1055
Leu Arg Ile Lys His Gln Gly Leu Gly Val Pro Ala Glu Leu Met Ala
        1060                1065                1070
Gln Met Phe Glu Glu Asp Asn Lys Glu Gln Ser Glu Glu Gly Leu Ser
        1075                1080                1085
Leu Leu Val Ser Arg Asn Leu Leu Arg Leu Met Asn Gly Asp Val Arg
        1090                1095                1100
His Leu Arg Glu Ala Gly Val Ser Thr Phe Ile Ile Thr Ala Glu Leu
1105                1110                1115                1120
Ala Ser Ala Pro Thr Ala Met Gly Gln
        1125
```

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gaatgaagaa cagatgaagc                                              20

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
ttgtcccatt gctgttggag c                                            21

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
gcgggaagct gctctagata accagattgg                                   30

<210> SEQ ID NO 6
<211> LENGTH: 4
<212> TYPE: DNA
<213> ORGANISM: Artificial Sequence
<220> FEATURE:
<223> OTHER INFORMATION: Primer

<400> SEQUENCE: 6 agtt                                                                4

-continued

```
<210> SEQ ID NO 7
<211> LENGTH: 4
<212> TYPE: DNA
<213> ORGANISM: Artificial Sequence
<220> FEATURE:
<223> OTHER INFORMATION: Primer

<400> SEQUENCE: 7 gctc                                                                4

<210> SEQ ID NO 8
<211> LENGTH: 6
<212> TYPE: DNA
<213> ORGANISM: Artificial Sequence
<220> FEATURE:
<223> OTHER INFORMATION: Primer

<400> SEQUENCE: 8 tctaga                                                              6
```

NUCLEIC ACID MOLECULES ENCODING HYPERACTIVE MUTANT PHYTOCHROMES AND USES THEREOF

FIELD OF THE INVENTION

This invention relates to the concept of functionally hyperactive red/far-red light sensor genes such as a modified phytochrome A (PHYA) nucleic acid molecule of which a serine/threonine amino acid at the hinge region between the amino- and the carboxy-domains and at the N-terminal serine/threonine cluster of phytochrome for Pr/Pfr-dependent phosphorylation/dephosphorylation was substituted with alanine. The phytochrome A functions as the photoreceptor in far-red wavelength light in mediating the suppression of shade avoidance and the greening of leaves. These modified phytochromes lacking critical serine/threonine residues for phosphorylation are hyperactive under far-red light. Another group of the modified phytochromes with bathochromic shift in their Pr-absorption band greatly is to provide an enhanced far-red sensitivity of plants growing under canopy and shade conditions. The present invention also provides the methods and processes for generating transgenic higher plants transformed with the said nucleic acid molecule to engineer internode elongation of economically important crop plants.

BACKGROUND OF THE INVENTION

Figure 1:
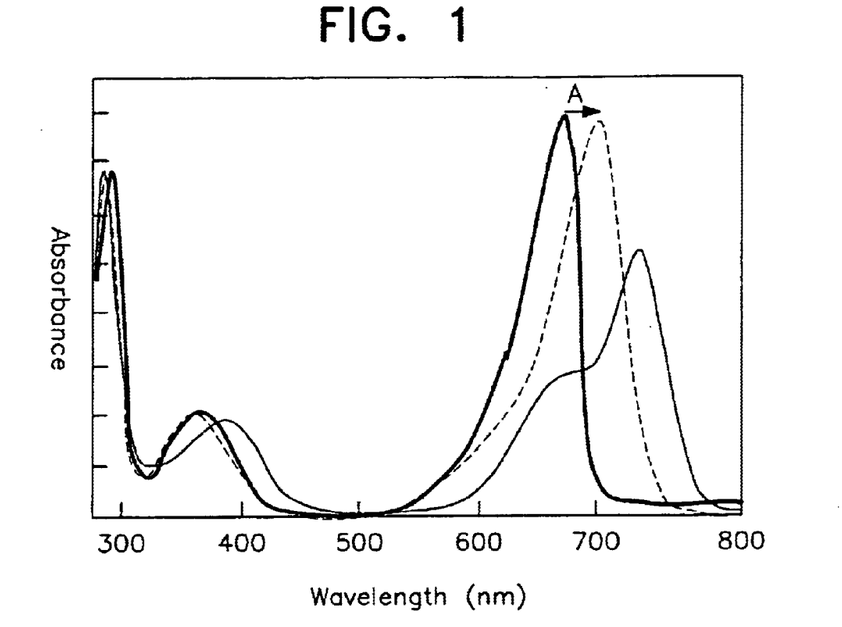
FIG. 1 shows the illustration of the bathochromic shift of the Pr-absorption spectrum. Note that the Pr form of phytochrome now strongly absorbs far-red light of wavelength longer than 700 nm.
Figure 2A:
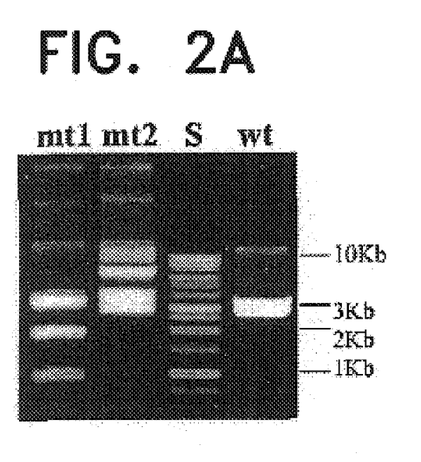
Figure 2B:
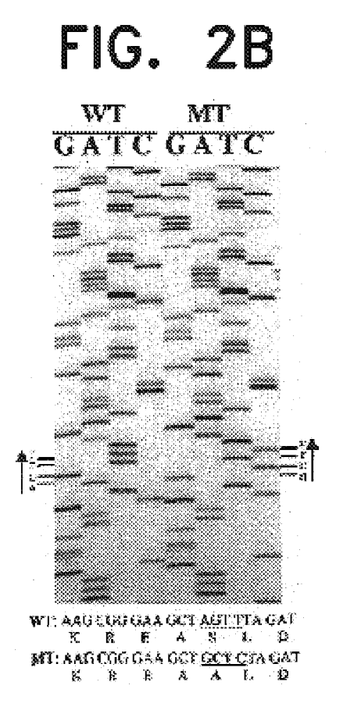

Phytochrome is a photoreceptor that control diverse aspects of growth and development in higher plants. Upon irradiation, the photoreceptor undergoes reversible interconversion between biologically inactive, red-absorbing phytochrome (Pr) and biologically active, far-red light absorbing phytochrome (Pfr) that enables it act as a molecular light switch. Photoconversion into Pfr form by red light treatment triggers its nuclear translocation from cytosol, initiating signaling that alters gene expression and thereby growth and development of plants. There are two photoisomers, red light ($\lambda$max=660 nm) absorbing form (designated to Pr) and far-red light ($\lambda$max=730 nm) absorbing form (designated to Pfr). Particularly, the absorption spectra of phytochrome are near the spectrum of canopy (FIG. 1, Neff et al, 2000). This spectral property shows it is directly related to shade avoidance. The initiation of shade avoidance depends on low R (red): FR (far red light) ratio. Low R: FR ratio accelerates not only the shade avoidance reaction that involves hypocotyls elongation, but also early flowering that causes immature fruit developments (Smith & Whitelam, 1997).

The photoreceptor consists of a 116–127 kDa apoprotein and a covalently attached linear tetrapyrrole chromophore. In plants, the apoproteins are encodes by a small gene family, e.g., five members PHYA-E in *Arabidopsis*. Molecular genetic analysis revealed that individual members of phytochromes play overlapping but distinct physiological roles. PHYA, a type 1 photo-labile phytochrome, controls very low fluence response and FR-high irradiance response, while type 2 phytochrome, encoded by PHYB-E, abundant in light-grown tissues, regulates low fluence responses (Quail et al., 1995; Neff et al., 2000).

Previously, oat PhyA was shown to undergo post-translational modification after red-light treatment, including phosphorylation at serine $598^{th}$ residue (Lapko et al., 1999). The Pfr-specific phosphorylation at serine $598^{th}$ residue suggested a regulatory role of this residue on photosensory signalling. To test the possibility, in the present invention, we performed site-directed mutagenesis with oat PHYA, substituting serine $598^{th}$ to alanine (designated S598A PHYA in the invention). The biological activity of mutated PHYA was compared with wild type PHYA by overexpression into phyA-null mutant of *Arabidopsis*. Under FR light condition, both wild type PHYA and S598A PHYA could complement phyA-deficient mutant, showing FR-high irradiance response. However, at adult stage, transgenic *Arabidopsis* plants overexpressing S598A PHYA exhibited shortened internode in adult plants and shortened petiole, whereas transgenic plants overexpressing wild type PHYA did not show any noticeable defect in adult morphology. Overexpression of PP2A gene resulted in a suppressed internode phenotype similar to that of S598A mutant phytochrome. Thus, we include in the invention the overexpression of PP2A gene as being equivalent to bona fide hyperactive phytochrome by keeping it dephosphorylated in vivo. These results indicate that S598A PHYA is more biologically active than wild type PHYA at least in the regulation of internode elongation.

Serine-to-alanine substitutions at the N-terminal serine/threonine cluster in phytochromes result in hyperactive phytochromes in *Arabidopsis thaliana* (Stockhaus et al., 1992). Among the N-terminal serine residues, serine-7 is the only residue in the cluster that is specifically autophosphorylated or phosphorylated by a phytochrome kinase in vivo (Lapko et al., 1997). Thus, S7A mutant phytochrome is a hyperactive phytochrome.

It has been possible to locate the active site of the autophosphorylating phytochrome A (acting as a "phytochrome kinase"). The PAS-related domain in the C-terminal half of the protein contains active site residues. Mutation or deletion of these residues is expected to result in hyperactivity of phytochrome A in vivo, since such mutants cannot autophosphorylate the protein.

By using the method of site-directed mutagenesis (Bhoo et al., 1997) and DNA shuffling, we have also generated phytochrome A mutants that absorb far-red shade light more effectively than wild type. This was achieved by substituting critical amino acid residues (for example, isoleucine-80) within the chromophore binding crevice of phytochrome A. FIG. 1 illustrates how a few nanometer red shift of the Pr-absorption band, so that it can absorb canopy and shade lights several orders of magnitude more effectively in the far-red wavelength than with the overexpression of wild type phytochrome. We propose that the far-red spectral action spectrum for the induction of seed germination (Shinomura et al., 1996) is consistent with the Pr-absorption spectrum of "hot band" or "twisted" chromophore conformation origin, the bathochromic mutant phytochromes are hyperactive in the responses of higher plants to far-red light.

This invention can be practically applied to control growth and development in general and internode elongation and leaf greening of higher plants in particular (Smith and Whitelam, 1997). The higher plants referred to here are those economically important in agriculture and horticulture. As used herein, the term "economically important higher plants" refers to higher plants that are capable of photosynthesis and widely cultivated for commercial purpose. The term "plant cell" includes any cells derived from a higher plant, including differentiated as well as undifferentiated tissues, such as callus and plant seeds.

SUMMARY OF THE INVENTION

The present invention relates to nucleic acid molecules encoding modified phytochrome A (PHYA) protein of which $598^{th}$ serine amino acid for Pfr-dependent phosphorylation was substituted by alanine. Such nucleic acid molecules preferentially encode a protein with the amino acid sequence as given in SEQ ID NO: 2. The mutant phytochrome A displays hypersensitive biological activity in the response of higher plants to far-red wavelength light.

The present invention extends to other mutant phytochromes that exhibit similar hyperactivity in the far-red spectral region and under canopy/shade light conditions. Such mutant phytochromes include $7^{th}$ serine-to-alanine mutants, PAS-related domain substitution/deletion mutants, and also the spectral mutants that absorb far-red light effectively.

Also, provided includes an uninterrupted gene sequence encoding the S598A PHYA, a nucleic acid fragment that can be directly ligated into recombinant DNA constructs, and the S598A PHYA expression vectors that can be readily used to transform cells of higher plants according to the present invention.

Provided also are transgenic higher plants that are readily accessible to the *Agrobacterium*-mediated transformation. Overexpression of the S598A PHYA gene results in shortened internodes. These phenotypic traits can be exploited in a way that higher plants of interest harboring the S598A PHYA gene exhibit dwarfism, a very important commercial trait in horticulture and agriculture.

Therefore, the present invention provides: 1. Nucleic acid molecules encoding a polypeptide of a modified oat phytochrome A (PHYA) of which $598^{th}$ serine amino acid for Pfr-dependent phosphorylation was substituted by alanine, comprising a nucleotide sequence as given in SEQ ID NO: 1.

BRIEF DESCRIPTION OF THE FIGURES

FIG. 2A and FIG. 2B show site-directed mutagenesis of oat phytochrome A. The $598^{th}$ serine residue, a target of Pfr-dependent phosphorylation was changed to alanine. After mutagenesis, XbaI digestion was performed to get a correct mutant gene (A). mt1 and mt2 are two different clones after mutagenesis, and wt is oat wild-type phyA gene in the vector. S is Promega 1 kb DNA ladder (G571 1). Some DNA sizes of 1 kb DNA ladder are indicated. A XbaI site at 1798bp was created during the mutagenesis. So, there are 3 fragments in the WT, 2820bp, 525bp and 3330bp, whereas there are 4 fragments in the MT, 1760bp, 951bp, 525bp and 3330bp. At the bottom of the FIG. 2A, 525bp band was shown. From the results, m1 clone showed the right restriction pattern and was further confirmation by DNA sequencing. B. DNA sequencing gel showing the changes of bases. WT sequence 5'-AGTT-3' was changed to 5'GCTC-3', which changed the Serine at 598 to Alanine.

FIG. 3A and FIG. 3B show transgene expression of wildtype PHYA and S598A PHYA. FIG. 3A. RT-PCR. The arrow showed the amplified bands of C-terminus DNA fragment of oat phyA (581bp).

FIG. 5A and FIG. 5B show adult morphology of transgenic plants. FIG. 5A. The morphology of representative plants grown under longa-day condition for 5 weeks. FIG. 5B. The average heights of plants grown under long day condition for 6 weeks. Each measurement was done with at least 12 plants.

DETAILED DESCRIPTION OF THE INVENTION

Phytochromes are the best characterized photoreceptor that regulate diverse aspects of growth and development in higher plants. Upon irradiation, it exhibits interconvertible photo-conversion between biologically inactive Pr (red absorbing phytochrome) form and biologically active Pfr (far-red absorbing phytochrome) form that enables it to act as a molecular light switch (Butler et al., 1959). The activated Pfr triggers downstream signaling that result in diverse photo-responses. Upon Pfr formation after red light absorption, phytochrome undergoes several conformational changes. The Pfr-chromophore is more exposed than the Pr-chromophore (Park et al., 2000). The N-terminal domain is more exposed in the Pr form than in the Pfr form. The hinge region is preferentially exposed in the Pfr form. These conformational changes would trigger downstream signaling events. Phosphorylation is a primary mechanism that transduces signaling in eukaryotes. Phytochrome signaling involves several phosphorylation events. Phytochrome itself exhibited Ser/Thr kinase activity (Yeh and Lagarias, 1997). PKS1, one of the phytochrome interacting factors including PIF3 and NDPK2 have been phosphorylated by phytochrome (Fankhauser, et al., 1999). Interestingly phytochrome is also phosphorylated in a Pfr-dependent manner. The $598^{th}$ Serine residue is preferentially phosphorylated in the Pfr form in vivo (Lapko et al., 1999). In vitro kinase assay showed that the $598^{th}$ serine was shown to be important for the light-regulation of autophosphorylation/phosphotransfer activity of phytochrome. As an effort to characterize the biological role of phosphorylation at $598^{th}$ serine of phytochrome in vivo, we performed site-directed mutagenesis and generated mutant PHYA of which $598^{th}$ serine was substituted by alanine. After generation of transgenic plants that overexpress wildtype PHYA or mutant PHYA using phyA-null *Arabidopsis* mutant, the phenotypes of transgenic plants were examined.

Figure 3A:
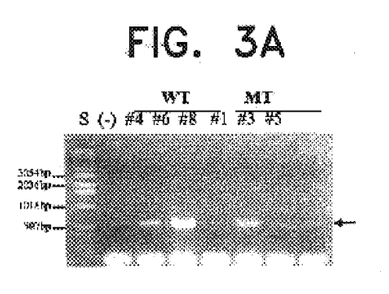
Figure 3B:
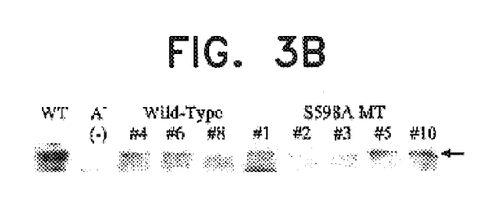
FIG. 3B. Western blot analysis. 50 ug of each protein sample was used for this analysis. The arrow showed the protein band of phyA. Lane WT, protein sample from wild-type *Arabidopsis thaliana* (positive control); lane A, protein sample from wild-type *Arabidopsis thaliana* phyA-201 mutant (negative control); the number represents independent transgenic seed lines of WT and MT; lane S, DNA standard (Gibco 1 kb ladder, 15615-016).

Using immunoblot analysis, we identified transgenic lines that overexpress foreign gene, PHYA or mutant PHYA (FIG. 3A and FIG. 3B). Two lines of wildtype PHYA overexpressing lines, designated as WT #4 and WT #6, and several lines of S598A PHYA overexpressing lines were chosen for further analysis.

Figure 4:
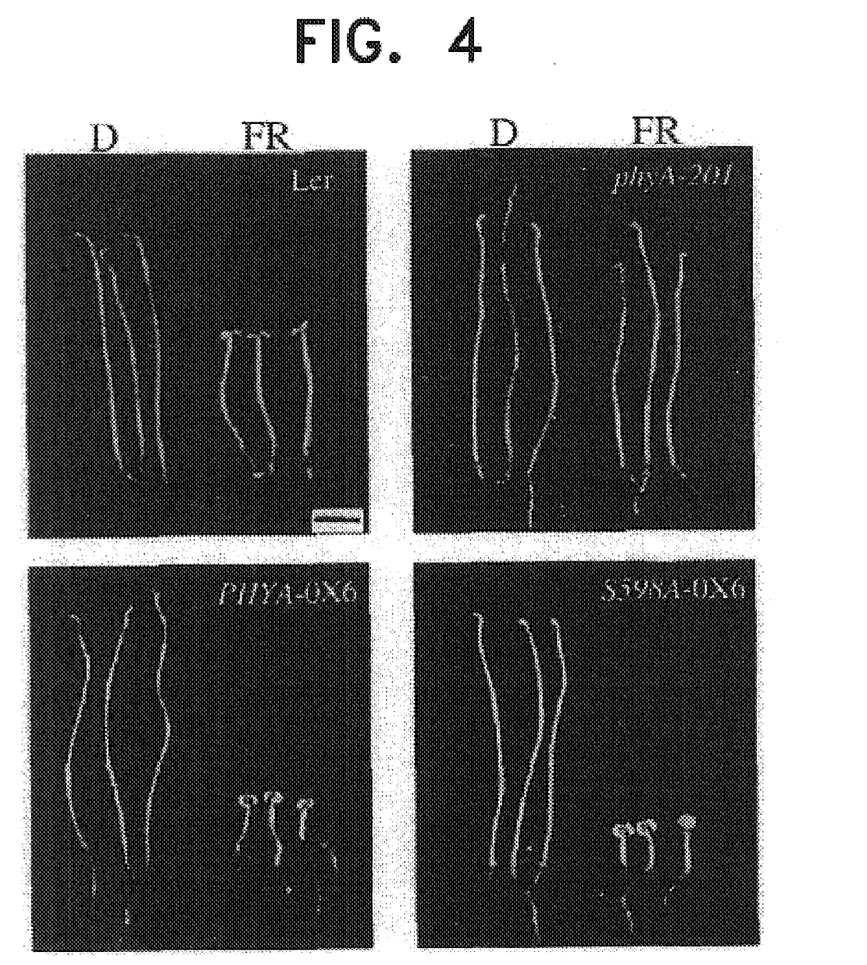
FIG. 4 shows FR-high irradiance response of transgenic seedlings. The seedlings were grown on MS media for 4 days in darkness or under FR light. The scale bar indicates 5 mm.

To test whether introduced PHYA is biologically functional in *Arabidopsis*, we grew seedlings under FR light or in the dark. As shown in FIG. 4, Ler wild type showed typical FR-responses, including shortened hypocotyl, expanded cotyledons, while phyA-null mutant exhibited skotomorphogenic development, such as long hypocotyl, closed cotyledons. The WT#4 and WT#6 transgenic seedlings showed typical light-dependent photomorphogenic development. Under the same condition, S598A PHYA transgenic lines complemented phyA null mutant, exhibiting FR-dependent photomorphogenic development. These results indicate that S598A PHYA is functional, complementing phyA-deficiency of phyA-201 mutant in *Arabidopsis*.

Figure 5A:
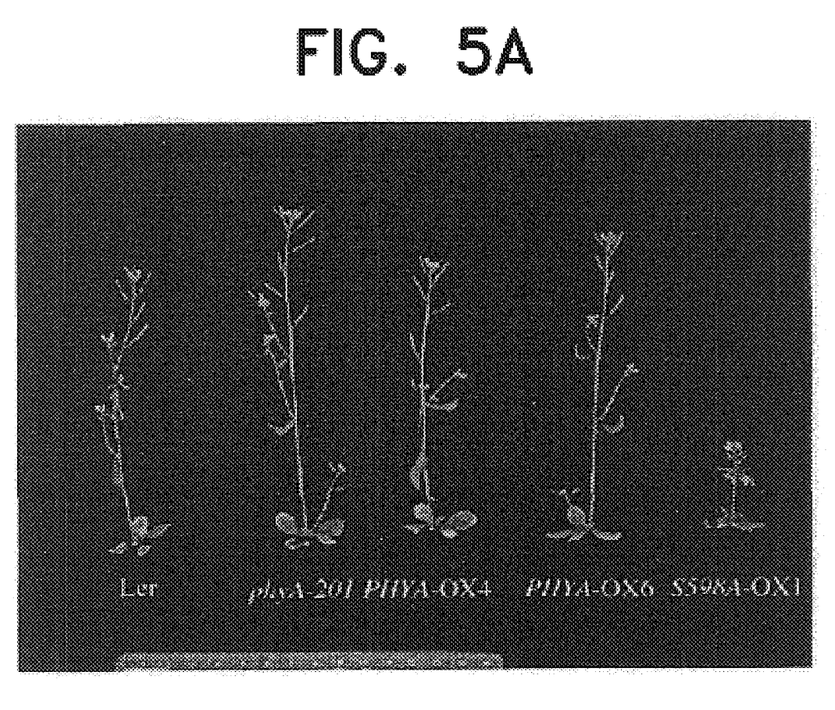
Figure 5B:
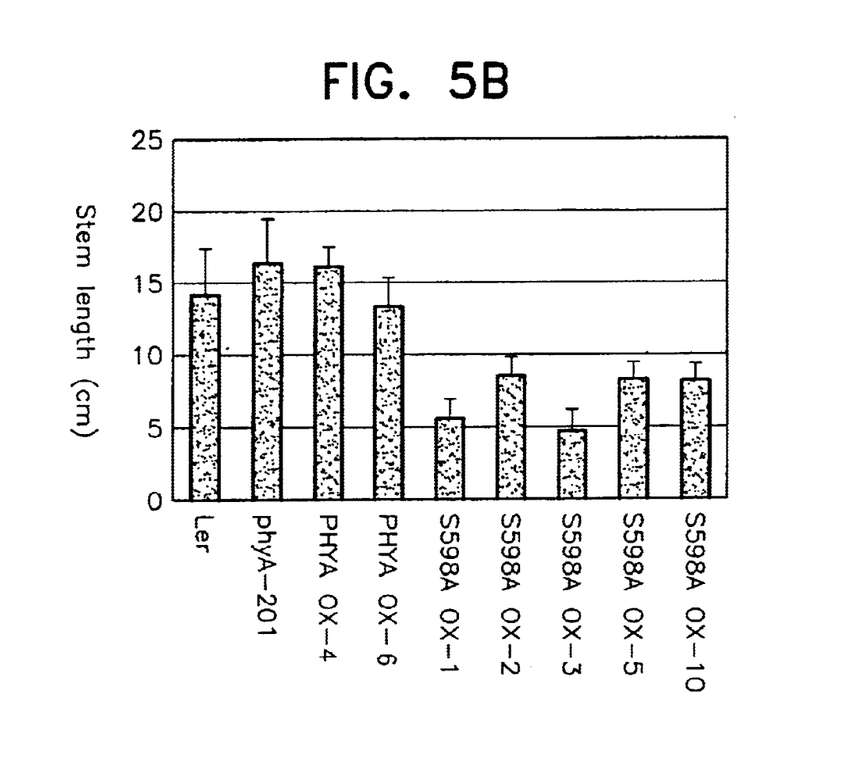

Previously oat PHYA was shown to be active in several dicot plants (Boylan and Quail, 1989; Boylan and Quail, 1991), mediating FR-HIR. In *Arabidopsis*, transgenic lines that overexpressing PHYA did not show any effects on adult morphology, while transgenic lines of tobacco and tomato exhibited several agronomic important traits such as dwarfism. When we grew the transgenic *Arabidopsis* plants that overexpress S598A PHYA, the transgenic lines showed dwarfism, while transgenic lines of PHYA were normal, compared to wild type (FIG. 5). The results suggest that S598A phyA is hyperactive to mediate adult dwarfism in *Arabidopsis*, compared to wildtype phyA. This trait is a potent agronomical target that can be applied to flowering plants to reduce cell/organ elongation resulting in improved agronomic values

EXAMPLES

Plant Materials and Growth Conditions

Seeds of pea plant was germinated and grown under sterile condition on the Murashige and Skoog (MS) media. The *Arabidopsis thaliana* ecotype Ler, phyA-201 mutants, and transgenic lines were grown on 0.5× MS medium. All *Arabidopsis* cultures were maintained in a controlled environment culture room at 26° C., 70% humidity and for the photoperiod of 16 hours. The *Arabidopsis* transformation was performed according to the simplified floral dip method, a well known technique to the art. For FR-high irradiance response, growth chamber (model E-30LED1; Percival Scientific, Inc., Boone, Iowa) equipped with FR light-emitting diode was used.

Enzymatic Treatments of DNA

DNA manipulations were carried out according to the standard procedures with some modifications whenever required. Restriction enzyme digestions were routinely done in 20 µl reaction volumes with an enzyme of 1–5 units per microgram DNA, and the mixtures were incubated at an appropriate temperature for 1–2 hours. Restriction enzyme digestion buffers used were those supplied by the manufacturer for each particular enzyme, unless specified otherwise. For ligation reactions, DNA fragments, either a digestion mixture or a PCR product, were first separated on 0.8–1.5% agarose gels, depending on the sizes of the DNA fragments of interest, and the desired DNA fragment was purified from the gel piece using either the GENECLEAN II Kit (BIO 101, Vista, USA) or the Gel Extraction Kit (Omega Biotek, Doraville, USA). Ligations were performed usually at the molar ratio of 1:1 to 1:3 in a 10 µl volume using the buffer supplied by the manufacturer, and the mixture was incubated at 13–16° C. for 10 minutes (for sticky-end ligations) or 30 minutes (for blunt-end ligations). T4 DNA ligase and its corresponding ligase buffer (NEB, Beverly, Mass., USA) were routinely used with 5–10 units of ligase in a 10 µl volume reaction. Polymerase chain reaction (PCR) was usually carried out 25 cycles, each with 1 minute denaturation at 94° C., 1 minute annealing at 60° C., and polymerization at 72° C. for 2 minutes per 1000 bases using the Pfu polymerase. For quantitative analysis, PCR was run 15–20 cycles, depending the gene expression levels, using the Taq polymerase (Promega, Madison, Wis.).

E. coli Transformation

For general cloning purpose, *E. coli* strain XL1-blue was routinely used as host cells for the transformation with plasmid DNAs. The competent *E. coli* cells were prepared in the laboratory and usually had an efficiency of $5 \times 10^{-6}$ to $10^{-7}$ colonies per µg control vector DNA. Three to five microliter of the ligation mixture was usually used to transform 100 µl of the competent *E. coli* cells. After incubation on ice for 20 minutes, the cell-DNA mixture was heat-shocked at 42° C. for 1 minute, and 1 ml of SOC medium was added. The mixture was then gently rotated at 37° C. for 1 hour to render the cells recovered from damage, and 50–300 µl was spread on LB plates containing an appropriate antibiotic. The plates were incubated at 37° C. overnight or until positive colonies were visible.

Plasmid Isolation and Purification

Vector DNA was isolated routinely by the alkaline-SDS method from *E. coli* culture. A 1 ml (for high copy number plasmid) or a 10 ml LB-ampicillin culture (for low copy number plasmid) was routinely prepared for the small scale purification of plasmid DNA. For the large scale purification, TB medium (Terrific broth, 47.6 grams of TB mix per liter, Difco, Detroit, USA) which gives higher plasmid DNA yields, instead of LB medium, was used. To prepare plasmid DNA for DNA sequencing and *Agrobacterium* transformation, those isolated by the alkaline-SDS method was further purified using the Plasmid Miniprep Kit II (Omega Biotek, Seoul, KOREA).

The Expression of the Genes and Proteins in the Transgenic Plants

After the screening of the transgenic plants, RT-PCR technique was used to confirm the transcription of the introduced gene. Total RNAs from the transgenic seedlings were prepared by using RNeasy® Plant mini kit (Qiagen, 74903) and followed the standard procedure to generate cDNA by MMRV-reverse transcriptase (Strategene). 5 µg of total RNA was used for the cDNA synthesis. After the synthesis of the cDNA, PCR was performed to confirm the expression of the genes in the transgenic plants. The used primers were 5'-GAATGAAGAACAGATGAAGC-3' (SEQ ID NO: 3) and 5'-TTGTCCCATTGCTGTTGGAGC-3' (SEQ ID NO: 4). The products are the C-terminal gene fragments of oat phyA whose size is 581 base pairs. To check the expression of WT and MT proteins and the amounts, the western blot analysis was performed. The preparation of protein samples from the transgenic plants was done as follows: about 4 leaves from each plant were taken off before bolting, put the leaves between the water-soaked Whatman filter papers, and incubated the leaves for at least 12 hours under dark condition. The leave samples were grinded in the microcentrifuge tubes using sea sands and plastic rods. This protein extraction procedure were performed on the ice or in the cold room under the green light condition, and the used buffer for the protein extraction composed of 70 mM Tris (pH 8.3), 35% ethylene glycol, 98 mM $(NH_4)_2SO_4$, 7 mM EDTA, 14 mM Sodium metabisulfite, 0.07% polyethyleneimine and 2.8 mM PMSF (all from Sigma except ethylene glycol that is from Fisher). The extracted protein samples were centrifuged at 14,000 rpm and 4° C. for 15 min, and the supernatant were used as protein samples for the western blot analysis. The protein samples were quantified by using Bio-Rad protein assay kit (500-0001), and 50 ug of protein samples were loaded onto the 10% SDS-PAGE gels for the western blot analysis. The protein bands on the SDS-PAGE gel were transferred to PVDF membrane (Hybond-P, Amersham Phamacia Biotech), and the membrane was incubated with oat phyA-specific monoclonal antibody, oat22 and oat25, for 2 hours and developed by using ECL™ western blotting analysis system purchased from Amersham Phamacia Biotech (RPN 2108). For the detection of *Arabidopsis* phyA, P25 and mAA7 antibodies were added to the reaction.

Site-Directed Mutagenesis of S598A Oat PHYA

The full size of cDNA encoding Avena phytochrome A (phyA) from pFY 122 (Boylan and Quail, 1989) was cloned to pGEM®-11zf(+) (Promega P2411) by digesting with BamHI and EcoRI. After purifying the pGEM®-11zf(+) plasmids containing full-length oat phyA cDNA, the site-directed mutagenesis in order to create Ser598Ala Avena phyA mutant was performed by using GeneEditor™ in vitro site-directed mutagenesis system (Promega Q9280). The oligonucleotide sequence of mutagenic primer for the mutagenesis is phosphorylated-5'-GCGGGAAGCTGCT CTAGATAACCAGATTGG-3' (SEQ ID NO: 5). The bold and italic bases are the mutagenized ones from the original sequence 5'-AGTT-3' (SEQ ID NO: 6) to 5'-GCTC-3' (SEQ ID NO: 7), and the underlined sequence, 5'-TCTAGA-3' (SEQ ID NO: 8) is a created XbaI restriction site which is used for the screening of the mutant gene. This new restriction site (XbaI) was introduced by silent mutation near the position to be mutated, allowing rapid and efficient screening for the mutant phyA (Ser598Ala mutant). After the mutagenesis, the mutagenized plasmids were purified and confirmed by XbaI digestion and DNA sequencing. DNA sequencing was done by using Sequenase version 2.0 DNA sequencing kit (Amersham, USB, US70770) with $^{35}$S-ATP.

DNA Sequencing and Sequence Analysis

All cDNA and DNA fragments and the junctions of the expression vector constructs were confirmed by direct DNA sequencing on both strands. DNA sequencing was carried out using the ABI PRISM 310 Genetic Analyzer (Perkin Elmer, Foster City, USA) as described in the manufacturer's manual. For each sequencing run, about 500 ng of plasmid DNA and 2–4 picomoles of 15–17 mer sequencing primer were used. Computer-assisted sequence analysis was performed using the BLAST program (NCBI, USA).

Gel Electrophoresis of DNA

Agarose gel electrophoresis of DNA was usually performed using gels with a concentration range of 0.8–1.5%, depending on the size of the DNA fragments to be analyzed, using the TAE buffer (40 mM Tris-acetate, 1 mM EDTA, pH 8.0). Electrophoresis was performed at a constant voltage rage of 50–200, depending on the amount of DNA loaded onto wells, for a desired time or until DNA fragments were well separated. The gel was stained with 0.5 µg/ml ethidium bromide solution, visualized on an UV transilluminator, and photographed if required.

Construction of Plant Expression Vectors

The wild-type (WT) and Ser598Ala mutant (MT) genes were subcloned into the plant transformation vector, pBI121 (Clontech, Cat No. 6018-1: 13 Kb, CaMV 35S promoter etc.). For the subcloning, the vector (pBI121) was digested with BamHI and EcoICRI, and the WT and MT genes in pGEM®-11zf(+) were eluted by sequential enzyme treatment: EcoRI digestion, T4 polymerase treatment for making blunt ended DNA and BamHI digestion. Since the vector and the genes have one blunt end and one cohesive end, they can be ligated and subcloned. After the subcloning and confirmation of the genes in pBI121, the purified plasmids were used for the transformation into phyA deficient *Arabidopsis thaliana*. Since the vector has a kanamycin-resistant gene, the seeds having the transformed genes were selected by geminating on the agar plate containing 50 µg/ml kanamycin.

References

Bhoo S. H., Hirano T., Jeong H. Y., Lee J. G., Furuya M. & Song P. S. (1997) Phytochrome photochromism probed by site-directed mutations and chromophore esterification. J. Am. Chem. Soc., 119, 11717–11718

Boylan M. T. and Quail P. H. (1989) Oat phytochrome is biologically active in transgenic tomatoes. Plant Cell, 1, 765–773.

Boylan, M. T. and Quail, P. H. (1991) Phytochrome A overexpression inhibits hypocotyl elongation in transgenic *Arabidopsis*. Proc. Natl. Acad. Sci. USA, 88, 10806–10810.

Fankhauser, C., Yeh, K. C., Lagarias, J. C., Zhang, H., Elich, T. D., and Chory, J. (1999). PKS1, a substrate phosphorylated by phytochrome that modulates light signaling in *Arabidopsis*. Science 284, 1539–1541.

Lapko, V. N., Jiang, X. Y., Smith, D. L., and Song, P. S. (1997). Posttranslational modification of oat phytochrome A: Phosphorylation of a specific serine in a multiple serine cluster. Biochemistry, 36, 10595–10599.

Lapko, V. N., Jiang, X. Y., Smith, D. L., and Song, P. S. (1999). Mass spectrometric characterization of oat phytochrome A: Isoforms and posttranslational modifications. Protein Science, 8, 1032–1044.

Neff, M. M., Fankhauser, C., and Chory, J. (2000) Light: an indicator of time and place. Genes Dev. 14, 257–271.

Park, C. M., Bhoo, S.-H. and Song, P.-S. (2000) Interdomain crosstalk in the phytochrome molecules, Cell Dev. Biol., 11, 449–456.

Quail, P. H., Boylan, M. T., Parks, B. M., Short, T. W., Xu, Y., and Wagner, D. (1995) Phytochromes: Photosensory perception and signal transduction. Science, 268, 675–680.

Shinomura, T., Nagatani, A., Hanzawa, H., Kubota, M., Watanabe, M., and Furuya, M. (1996). Action spectra for phytochrome A- and B-specific photoinhibition of seed germination in *Arabidopsis thaliana*. Proc. Natl. Acad. Sci. USA, 93, 8129–8133.

Smith H. & Whitelam G. C. (1997) The shade avoidance syndrome: multiple responses mediated by multiple phytochromes. Plant, Cell & Environ. 20, 840–844

Stockhaus, J., Nagatani, A., Halfter, U., Kay, S., Furuya, M., and Chua, N.-H. (1992) Serine-to alanine substitutions at the amino-terminal region of phytochrome A results in an increase in biological activity. Genes Dev. 6, 2364–2372.

Yeh, K. C., and Lagarias, J. C. (1998). Eukaryotic phytochromes: light-regulated serine/threonine protein kinases with histidine kinase ancestry. Proc. Natl. Acad. Sci. USA 95, 13976–13981.

What is claimed is:

1. An isolated nucleic acid molecule encoding the modified phytochrome A, which is selected from the group consisting of:

(a) a nucleic acid molecule encoding the polypeptide with the amino acid sequence of SEQ ID NO: 2; and (b) a nucleic acid molecule comprising the coding region of the nucleotide sequence of SEQ ID NO: 1.

2. An expression vector for transformation of plant cells comprising:

(a) the polynucleotide of SEQ ID NO: 1 encoding a modified phytochrome A; and (b) regulatory sequences operatively linked to the polynucleotide such that the polynucleotide is expressed in the plant cell, wherein said expression results in hypersensitivity to light.

3. A transgenic plant cell transformed with the expression vector of claim 2.

4. A transgenic plant having shade tolerance regenerated from the transgenic plant cell of claim 3.

* * * * *